(12) United States Patent
Surburg et al.

(10) Patent No.: US 6,420,334 B1
(45) Date of Patent: Jul. 16, 2002

US006420334B1

(54) TETRACYCLIC ACETALS

(75) Inventors: Horst Surburg; Peter Wörner, both of Holzminden (DE)

(73) Assignee: Haarmann & Reimer GmbH, Holzminden (DE)

( * ) Notice: Subject to any disclaimer, the term of this patent is extended or adjusted under 35 U.S.C. 154(b) by 209 days.

(21) Appl. No.: 09/609,042

(22) Filed: Jun. 30, 2000

(30) Foreign Application Priority Data

Jul. 8, 1999 (DE) .......................................... 199 31 709

(51) Int. Cl.⁷ ................................................. A61K 7/46
(52) U.S. Cl. ................................. 512/25; 512/8; 512/9; 512/11; 512/13; 512/26; 512/27; 549/330; 549/331; 549/356; 549/381; 549/385; 549/386; 549/396; 549/397; 549/398; 549/414
(58) Field of Search .............................. 512/25, 26, 27, 512/8, 9, 11, 13; 549/330, 331, 356, 381, 385, 386, 396, 397, 398, 414

(56) References Cited

U.S. PATENT DOCUMENTS

| | | | |
|---|---|---|---|
| 5,441,930 A | 8/1995 | Bruns et al. | 512/13 |
| 5,892,062 A | 4/1999 | Pickenhagen et al. | 549/432 |

OTHER PUBLICATIONS

J. Chem. Soc. Perkin Trans. I (month unavailable) 1983, pp. 1373–1378, McAndrews et al The Acetylation of Cedrene in the Presence of Titanium Tetrachloride.

*Primary Examiner*—Jill Warden
*Assistant Examiner*—Monique T. Cole
(74) *Attorney, Agent, or Firm*—Joseph C. Gil; Noland J. Cheung

(57) ABSTRACT

2-Alkoxydecahydro-2,3a,4,4,7-pentamethyl-3,7a-methano-7aH-indeno[5,6-b]furans are valuable novel woody fragrances for the preparation of perfume oils.

7 Claims, No Drawings

TETRACYCLIC ACETALS

FIELD OF THE INVENTION

Despite a large number of existing fragrances, there continues to be a need in the perfume industry for novel fragrances which as well as having their odoriferous properties additionally have positive secondary benefits, such as, for example, higher stability, better performance and effectiveness, better tenacity and long-lastingness.

SUMMARY OF THE INVENTION

We have found novel tetracyclic acetals of the two isomeric structures

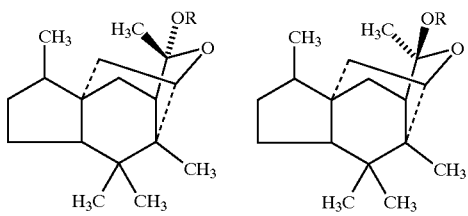

in which

R is a lower alkyl.

DETAILED DESCRIPTION OF THE INVENTION

The acetals are particularly suitable as fragrances, which can be used in perfuming.

Lower alkyl generally represents methyl, ethyl, n-propyl, iso-propyl, n-butyl or isobutyl.

Particular preference is given to methyl and ethyl.

The novel tetracyclic acetals are prepared in a manner known per se starting from alpha-cedrene, which is reacted with acetic anhydride in the presence of titanium tetrachloride as a relatively strong Lewis acid. This forms, not as in the case of the reaction with acidic catalysts such as, for example, phosphoric acid, "acetylcedrene" ("methyl cedryl ketone"), a fragrance which has long been widely used in the prepa-ration of perfumes, but, with a structural rearrangement and the addition of water, the tricyclic hydroxyketone 1-(octahydro-8-hydroxy-3,6,7,7-tetramethyl-3 a,6-ethano-3aH-inden-5-yl)-ethanone which, upon heating and with the elimination of water, is gradually converted into the tetracyclic enol ether decahydro-2-methylene-3 a,4,4,7-tetramethyl-3,7a-methano-7aH-indeno[5,6-b]furan. By adding water to the enol ether, the hydroxy ketone readily reforms with ring opening (see also. J. Chem. Soc. Perkin Trans. I 1983, pp. 1373–78).

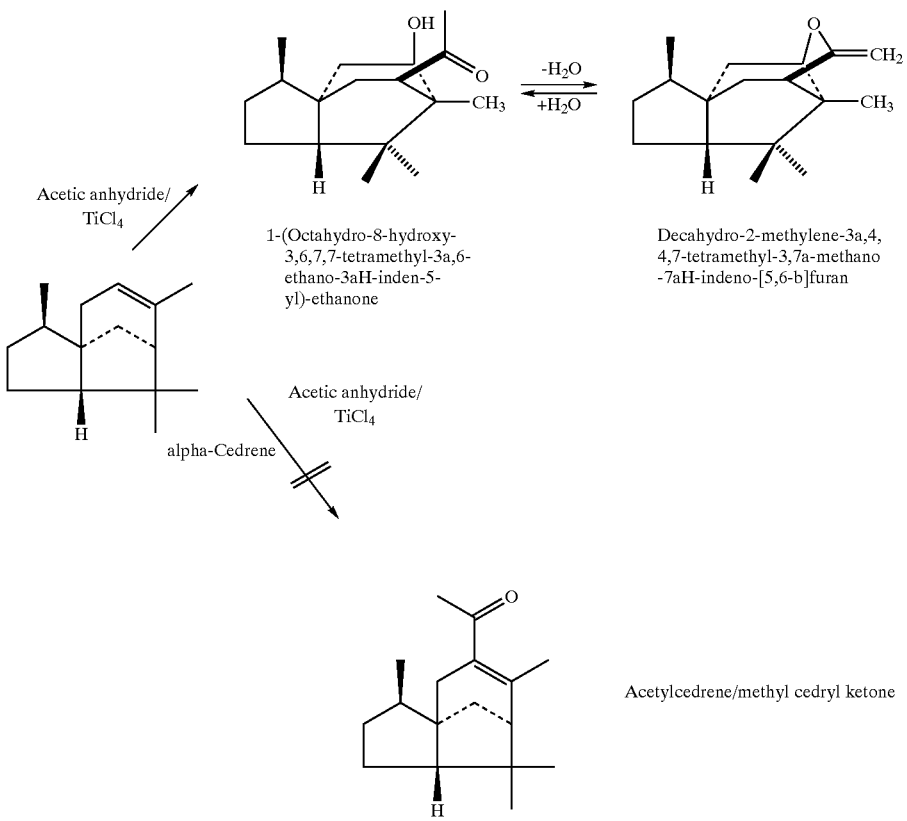

The hydroxy ketone is odorless in pure form; the enol ether has merely a weak odor reminiscent of the sesquiterpene hydrocarbon fraction of cedarwood oil ("Cedarwood oil terpenes").

Surprisingly, we have now found that alcoholic solutions of both the hydroxy ketone and of the enol ether have a strong characteristic woody odor which is not a characteristic of the two pure compounds. We found that the reason for this lies in the formation of novel, as yet undescribed tetracyclic acetals. The formation of these acetals is described by the two equations below:

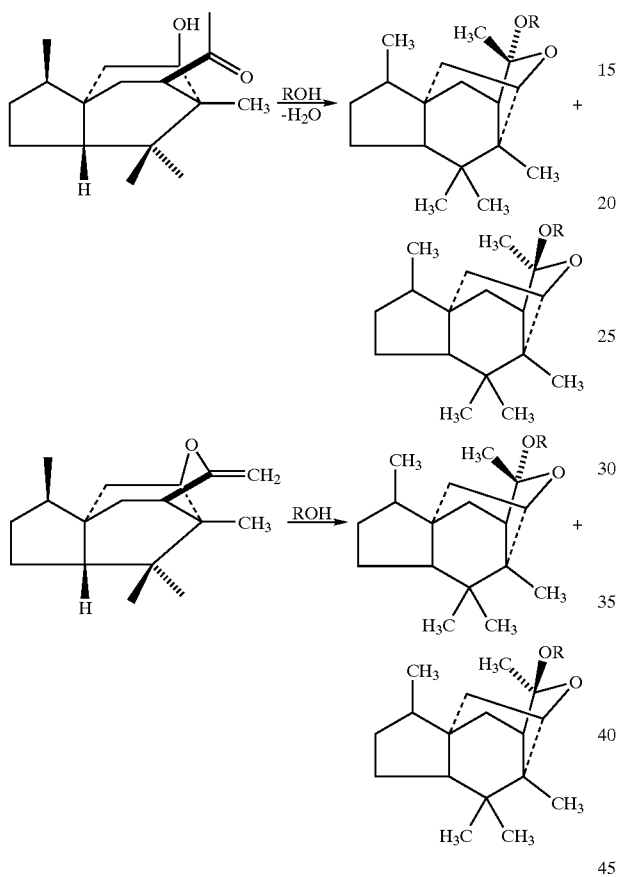

The acetals according to the present invention are generally in the form of the mixture of the two isomers.

Both isomers have a marked intensive and unusually long-lasting fresh woody odor.

Because of these particular organoleptic properties, these acetals are highly suitable for use as fragrance materials.

Details of how the preparation of the acetals according to the present invention are prepared are as follows:

The hydroxy ketone 1-(octahydro-8-hydroxy-3,6,7,7-tetramethyl-3a,6-ethano-3aH-inden-5-yl)-ethanone or the enol ether decahydro-2-methylene-3a,4,4,7-tetramethyl-3,7a-methano-7aH-indeno[5,6-b]furan or a mixture of the two is admixed with a lower alcohol, where, most preferably, the alcohol in question is used in excess and also serves as solvent. It is, however, also possible to add another inert solvent. The reaction can be carried out in a wide temperature range, e.g. between −25° and +150° C., optionally under pressure. Preference is given to a temperature range between 20° and 80° C.

After the excess alcohol, or other solvent, has been distilled off, the acetals according to the present invention are obtained as residues; where appropriate, the alcoholic solution can also be reused directly.

The acetals according to the present invention can be used as individual substances in a large number of products; it is particularly advantageous to combine them with other fragrance materials to give new types of perfume compositions.

By using the acetals according to the present invention it is generally possible to achieve, even at a low concentration, radiantly fresh, woody odor notes in the resulting perfume compositions, where the overall olfactory impression is harmonized to a striking degree, the radiance is perceptibly increased and the long-lastingness of the perfume oil is significantly increased.

Examples of fragrances with which the acetals according to the present invention can be advantageously combined can be found, for example, in S. Arctander, Perfume and Flavor Materials, Vols. I and II, Montclair, N.J., 1969, published privately or K. Bauer, D. Garbe and H. Surburg, Common Fragrance and Flavor Materials, $3^{rd}$ Ed., Wiley-VCH, Weinheim 1997.

Individual examples which may be mentioned are:

Extracts from natural raw materials such as essential oils, concretes, absolutes, resins, resinoids, balsams, tinctures, such as, for example, ambergris tincture; amyris oil; angelica seed oil; angelica root oil; anise seed oil; valerian oil; basil oil; tree moss absolute; bay oil; armoise oil; benzoin resin; bergamot oil; beeswax absolute; birch tar oil; bitter almond oil; savoury oil; bucco leaf oil; cabreuva oil; cade oil; calmus oil; camphor oil; cananga oil; cardamom oil; cascarilla oil; cassia oil; cassie absolute; castoreum absolute; cedar leaf oil; cedarwood oil; cistus oil; citronella oil; lemon oil; copaiva balsam; copaiva balsam oil; coriander oil; costus root oil; cumin oil; cypress oil; Davana oil; dill herb oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiacwood oil; gurjun balsam; gurjun balsam oil; helichrysum absolute; helichrysum oil; ginger oil; iris root absolute; iris root oil; jasmine absolute; calamus oil; camomile blue oil; camomile Roman oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lovage oil; distilled lime oil; expressed lime oil; rosewood oil; litsea cubeba oil; laurel leaf oil; mace oil; marjoram oil; mandarin oil; massoi bark oil; mimosa absolute; ambrette seed oil; musk tincture; clary sage oil; nutmeg oil; myrrh absolute; myrrh oil; myrtle oil; clove leaf oil; clove bud oil; neroli oil; olibanum absolute; olibanum oil; opopanax oil; orange-flower absolute; orange oil; origanum oil; palmarosa oil; patchouli oil; perilla oil; peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; sage oil Dalmatian; sage oil Spanish; sandalwood oil; celery seed oil; spike lavender oil; star anise oil; styrax oil; tagetes oil; fir needle oil; teatree oil; turpentine oil; thyme oil; Tolu balsam; tonka absolute; tuberose absolute; vanilla extract; violet leaf absolute; verbena oil; vetyver oil; juniper oil; wine lees oil; wormwood oil; wintergreen oil; ylang oil; hyssop oil; civet absolute; cinnamon leaf oil; cinnamon bark oil; and fractions thereof, or ingredients isolated therefrom;

individual fragrances from the group of hydrocarbons, such as, for example, 3-carene; α-pinene; β-pinene; α-terpinene; γ-terpinene; p-cymene; bisabolene; camphene; caryophyllene; cedrene; famesene; limonene; longifolene; myrcene; ocimene; valencene; (E,Z)-1,3,5-undecatriene; of aliphatic alcohols, such as, for example, hexanol; octanol; 3-octanol; 2,6-dimethylheptanol; 2-methyl-2-heptanol, 2-methyl-2-octanol; (E)-2-hexenol; (E)- and (Z)-3-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol; of aliphatic aldehydes and acetals thereof, such as, for example, hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-5,9-undecadienal; heptanal diethyl acetal; 1,1-dimethoxy-2,2,5-trimethyl-4-hexene; citronellyl oxyacetaldehyde; of aliphatic ketones and oximes thereof, such as, for example, 2-heptanone; 2-octanone; 3-octanone; 2-nonanone; 5-methyl-3-heptanone; 5-methyl-3-heptanone oxime; 2,4,4,7-tetramethyl-6-octen-3-one; of aliphatic sulphur-containing compounds, such as, for example, 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthene-8-thiol;

of aliphatic nitriles, such as, for example, 2-nonenenitrile; 2-tridecenenitrile; 2,12-tridecene-nitrile; 3,7-dimethyl-2,6-octadienenitrile; 3,7-dimethyl-6-octenenitrile;

of aliphatic carboxylic acids and esters thereof, such as, for example, (E)- and (Z)-3-hexenyl formate; ethyl acetoacetate; isoamyl acetate; hexyl acetate; 3,5,5-trimethyl-hexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate,; isoamyl butyrate; hexyl butyrate; (E)- and (Z)-3-hexenyl isobutyrate; hexyl crotonate; ethyl isovalerate; ethyl 2-methylpentanoate; ethyl hexanoate; allyl hexanoate; ethyl heptanoate; allyl heptanoate; ethyl octanoate; ethyl (E,Z)-2,4-decadienoate; methyl 2-octynoate; methyl 2-nonynoate; allyl 2-isoamyloxyacetate; methyl 3,7-dimethyl-2,6-octadienoate;

of the acyclic terpene alcohols, such as, for example, citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol; 2,6-dimethyl-2,5,7-octatrien-1-ol; and formates, acetates, propionates, isobutyrates, butyrates, isovalerates, pentanoates, hexanoates, crotonates, tiglinates, 3-methyl-2-butenoates thereof;

of acyclic terpene aldehydes and ketones, such as, for example, geranial; neral; cirtonellal; 7-hydroxy-3,7-dimethyloctanal; 7-methoxy-3,7-dimethyloctanal; 2,6,10-trimethyl-9-undecenal; geranylacetone; and the dimethyl and diethyl acetals of geranial, neral, 7-hydroxy-3,7-dimethyloctanal;

of cyclic terpene alcohols, such as, for example, menthol; isopulegol; alpha-terpineol; terpineol-4; menthan-8-ol; menthan-1-ol; menthan-7-ol; borneol; isobomeol; linalool oxide; nopol; cedrol; ambrinol; vetiverol; guaiol; and formates, acetates, propionates, isobutyrates, butyrates, isovalerates, pentanoates, hexanoates, crotonates, tiglinates, 3-methyl-2-butenoates thereof;

of cyclic terpene aldehydes and ketones, such as, for example, menthone; isomenthone; 8-mercaptomenthan-3-one; carvone; camphor; fenchone; alpha-ionone; betaionone; alpha-n-methylionone; beta-n-methylionone; alpha-isomethylionone; betaisomethylionone; alpha-iron; alpha-damascone; beta-damascone; beta-damascenone; delta-damascone; gamma-damascone; 1-(2,4,4-trimethyl-2-cyclohexen-1-yl)-2-bu-ten-1-one; 1,3,4,6,7,8a-hexahydro-1,1,5,5-tetramethyl-2H-2,4a-methanonaphthalen-8(5H)-one; nootkatone; dihydronootkatone; alpha-sinensal; beta-sinensal; acetylated cedarwood oil (methyl cedryl ketone);

of cyclic alcohols, such as, for example, 4-tert-butylcyclohexanol; 3,3,5-trimethyl-cyclohexanol; 3-isocamphylcyclohexanol; 2,6,9-trimethyl-Z2,Z5,E9-cyclododeca-trien-1-ol; 2-isobutyl-4-methyltetrahydro-2H-pyran-4-ol;

of cycloaliphatic alcohols, such as, for example, alpha-3,3-trimethyl-cyclohexyl-methanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)-hexan-3-ol;

of cyclic and cycloaliphatic ethers, such as, for example, cineol; cedryl methyl ether; cyclododecyl methyl ether; (ethoxymethoxy)cyclododecane; alpha-cedrene epoxide; 3a,6,6,9a-tetramethyldodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methylpropyl)-1,3-dioxane;

of cyclic ketones, such as, for example, 4-tert-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetra-methylcyclohexanone; 4-tert-pentylcyclohexanone; 5-cyclohexadecen-1-one; 6,7-dihydro-1,1,2,3,3-pentamethyl-4(5H)-indanone; 5-cyclohexadecen-1-one; 8-cyclohexadecen-1-one; 9-cycloheptadecen-1-one; cyclopentadecanone;

of cycloaliphatic aldehydes, such as, for example, 2,4-dimethyl-3-cyclohexene-carbaldehyde; 2-methyl-4-(2,2,6-trimethyl-cyclohexen-1-yl)-2-butenal; 4-(4-hydroxy-4-methyl-pentyl)-3-cyclohexenecarbaldehyde; 4-(4-methyl-3-penten-1-yl)-3-cyclohexenecarbaldehyde;

of cycloaliphatic ketones, such as, for example, 1-(3,3-dimethyl-cyclohexyl)-4-penten-1-one; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl-2,6,10-trimethyl-2,5,9-cyclododecatrienyl ketone; tert-butyl-(2,4-dimethyl-3-cyclohexen-1-yl)ketone;

of esters of cyclic alcohols such as, for example, 2-tert-butylcyclohexyl acetate; 4-tert-butylcyclohexyl acetate; 2-tert-pentylcyclohexyl acetate; 4-tert-pentylcyclohexyl acetate; decahydro-2-naphthyl acetate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5 or 6-indenyl acetate; 4,7-methano-3a,4,5,6,7,7a-hexahydro-5 or 6-indenyl propionate; 4,7-methano-3a,4,5,6,7,7a-hexahydro-5 or 6-indenyl isobutyrate; 4,7-methanooctahydro-5 or 6-indenyl acetate;

of esters of cycloaliphatic carboxylic acids, such as, for example, allyl 3-cyclohexylpropionate; allyl cyclohexyloxyacetate; methyl dihydrojasmonate; methyl jasmonate; methyl-2-hexyl-3-oxocyclopentanecarboxylate; ethyl 2-ethyl-6,6-dimethyl-2-cyclohexenecarboxylate; ethyl-2,3,6,6-tetramethyl-2-cyclohexenecarboxylate; ethyl 2-methyl-1,3-dioxolan-2-acetate;

of aromatic hydrocarbons, such as, for example, styrene and diphenylmethane; of araliphatic alcohols, such as, for example, benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids, such as, for example, benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate; the araliphatic ethers, such as, for example, 2-phenylethyl methyl ether; 2-phenylethyl isoamyl ether; 2-phenylethyl-1-ethoxyethyl ether; phenylacetaldehyde dimethyl acetal; phenylacetaldehyde diethyl acetal; hydrotropaldehyde dimethyl acetal; phenylacetaldehyde glycerol acetal; 2,4,6-trimethyl-4-phenyl-1,3-dioxane; 4,4a,5,9b-tetrahydroindeno[1,2-d]-m-dioxin; 4,4a,5,9b-tetrahydro-2,4-dimethyl-indeno[1,2-d]-m-dioxin;

of aromatic and araliphatic aldehydes, such as, for example, benzaldehyde; phenylacetaldehyde; 3-phenylpropanal; hydrotropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert-butylphenyl)propanal; 3-(4-tert-butylphenyl)propanal; cinnamaldehyde; alpha-butylcinnamaldehyde; alpha-amylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

of aromatic and araliphatic ketones, such as, for example, acetophenone; 4-methyl-acetophenone; 4-methoxyacetophenone; 4-tert-butyl-2,6-dimethylacetophenone; 4-phenyl-2-butanone; 4-(4-hydroxyphenyl)-2-butanone; 1-(2-naphthalenyl)ethanone; benzophenone; 1,1,2,3,3,6-hexamethyl-5-indanyl methyl ketone; 6-tert-butyl-1,1-dimethyl-4-indanyl methyl ketone; 1-[2,3-dihydro-1,1,2,6-tetramethyl-3-(1-methyl-ethyl)-1H-5-indenyl]ethanone; 5',6',7',8'-tetrahydro-3',5',5',6',8',8'-hex acetonaphthone;

of aromatic and araliphatic carboxylic acids and esters thereof, such as, for example, benzoic acid; phenyl acetic acid; methyl benzoate; ethyl benzoate; hexyl benzoate; benzyl benzoate; methyl phenylacetate; ethyl phenylacetate; geranyl phenylacetate; phenylethyl phenylacetate; methyl cinnamate; ethyl cinnamate; benzyl cinnainate; phenylethyl cinnamate; cinnamyl cinnamate; allyl phenoxyacetate; methyl salicylate; isoamyl salicylate; hexyl salicylate; cyclohexyl salicylate; cis-3-hexenyl salicylate; benzyl salicylate; phenylethyl salicylate; methyl 2,4-dihydroxy-3,6-dimethylbenzo-ate; ethyl 3-phenylglycidate; ethyl 3-methyl-3-phenylglycidate;

of nitrogen-containing aromatic compounds, such as, for example, 2,4,6-trinitro-1,3-dimethyl-5-tert-butylbenzene; 3,5-dinitro-2,6-dimethyl-4-tert-butylacetophenone; cinnamonitrile; 5-phenyl-3-methyl-2-pentenenitrile; 5-phenyl-3-methylpentanenitrile; methyl anthranilate; methyl N-methylanthranilate; Schiff bases of methyl anthranilate with 7-hydroxy-3,7-dimethyloctanal; 2-methyl-3-(4-tert-butylphenyl)-propanal or 2,4-dimethyl-3-cyclohexenecarbaldehyde; 6-isopropylquinoline; 6-isobutylquinoline; 6-sec-butylquinoline; indole; skatole; 2-methoxy-3-isopropyl-pyrazine; 2-isobutyl-3-methoxypyrazine;

of phenols, phenyl ethers and phenyl esters, such as, for example, estragole; anethole; eugenole; eugenyl methyl ether; isoeugenole; isoeugenyl methyl ether; thymole; carvacrol; diphenyl ether; beta-naphthyl methyl ether; beta-naphthyl ethyl ether; betanaphthyl isobutyl ether; 1,4-dimethoxybenzene; eugenyl acetate; 2-methoxy-4-methylphenol; 2-ethoxy-5-(1-propenyl)phenol; p-cresyl phenylacetate;

of heterocyclic compounds, such as, for example, 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

of lactones, such as, for example, 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecane-dioate; coumarin; 2,3-dihydrocoumarin; octahydrocoumarin.

The perfume oils comprising the acetals according to the present invention can be used for perfuming in liquid form, neat or diluted with a solvent. Suitable solvents for this purpose are, for example, ethanol, isopropanol, diethylene glycol monoethyl ether, glycerol, propylene glycol, 1,2-butyleneglycol, dipropylene glycol, diethyl phthalate, triethyl citrate, isopropyl myristate, etc.

In addition, the perfume oils comprising the acetals according to the present invention can be adsorbed on a carrier which serves both to distribute the fragrance finely within the product and to release it in a controlled manner during use. Such carriers can be porous inorganic materials, such as light sulphate, silica gels, zeolites, gypsums, clays, clay granules, gas concrete etc. or organic materials such as woods and cellulose-based substances.

The perfume oils comprising the acetals according to the present invention can also be in microencapsulated form, in spray dried form, as inclusion complexes or as extrusion products and are added in this form to the product to be perfumed.

The properties of the perfume oils modified in this way can optionally be further optimized by "coating" with suitable materials with regard to a more targeted fragrance release, for which purpose preference is given to using wax-like polymers such as, for example, polyvinyl alcohol.

Microencapsulation of the perfume oils can, for example, be carried out by the coacervation process using capsule materials made from, for example, polyurethane-like substances or soft gelatins. The spray-dried perfume oils can, for example, be prepared by spray drying an emulsion or dispersion comprising the perfume oil, where the carriers used can be modified starches, proteins, dextrin and vegetable gums. Inclusion complexes can be prepared, for example, by introducing dispersions of the perfume oil and cyclodextrins or urea derivatives into a suitable solvent, e.g., water. Extrusion products can be obtained by melting the perfume oils with a suitable wax-like substance and by extrusion with subsequent solidification, optionally in a suitable solvent, e.g. isopropanol.

In perfume compositions, the amount of acetals according to the present invention used is from 0.05 to 50% by weight, preferably from 0.5 to 20%, based on the overall perfume oil.

The perfume oils comprising the acetals according to the present invention can be used in concentrated form, in solutions or in the above-described modified form for the preparation of, for example, perfume extraits, eau de parfum, eau de toilette, aftershave, eau de colognes, pre-shave products, splash colognes and perfumed freshening wipes, and the perfuming of acidic, alkaline and neutral cleaners, such as, for example, floor cleaners, window cleaners, dishwashing detergents, bath and sanitary cleaners, scouring milk, solid and liquid WC cleaners, carpet cleaner foams and powders, liquid detergents, detergent powders, laundry pretreatment agents such as bleaches, soaking agents and stain removers, fabric softeners, washing soaps, washing tablets, disinfectants, surface disinfectants, and of air fresheners in liquid or gel form or deposited on a solid carrier, aerosol sprays, waxes and polishes, such as furniture polishes, floor waxes, shoe creams, and bodycare preparations, such as, for example, solid and liquid soaps, shower gels, shampoos, shaving soaps, shaving foams, bath oils, cosmetic emulsions of the oil-in-water, water-in-oil and water-in-oil-in-water type, such as, for example, skin creams and lotions, face creams and lotions, sunscreen creams and lotions, aftersun creams and lotions, hand creams and lotions, foot creams and lotions, depilatory creams and lotions, aftershave creams and lotions, tanning creams and lotions, haircare products, such as, for example, hair sprays, hair gels, hair setting lotions, hair rinses, permanent and semipermanent hair colorants, hair-shaping compositions, such as cold waves and hair-smoothing compositions, hair tonics, hair creams and lotions, deodorants and antiperspirants, such as, for example, armpit sprays, roll-ons, deodorant sticks, deodorant creams, products for decorative cosmetics, such as, for example, eyeshadows, nail varnish, make-up, lipsticks, mascara, and also candles, lamp oils, joss-sticks, insecticides, repellents, propellants.

A main use of the acetals according to the present invention, because of their stability in the alkaline range, is the perfuming of soaps and detergents. When used for perfuming detergents, the acetals according to the present invention are characterized by a substantivity which is increased compared with fragrances used hitherto, i.e. by increased tenacity and an increased long-lastingness of the fragrance on the washed fibre.

For the perfuming of the products described, the amount of perfume composition can be from 0.1 to 40% by weight, preferably from 0.5 to 20% by weight, based on the total product.

The invention is further illustrated but is not intended to be limited by the following examples in which all parts and percentages are by weight unless otherwise specified.

EXAMPLES

Example 1

Preparation of a Perfume Composition for use in an Eau-de-toilette for Men

The following components were mixed (all figures are parts by weight):

| | |
|---|---|
| Agrumex HC H&R | 20 |
| Ambroxide H&R | 5 |
| Benzyl salicylate | 150 |
| Citral | 15 |
| Citrylal H&R | 5 |
| CPD supra H&R 50% in TEC* | 20 |
| Coumarin | 10 |
| Dihydromyrcenol | 100 |
| Evernyl Givaudan-Roure | 5 |
| Fir balsam absolute | 15 |
| Freesiol H&R | 15 |
| Geranitril H&R | 5 |
| Hedion Firmenich | 40 |
| Hexyl salicylate | 25 |
| Isoananate H&R | 5 |
| Isobornyl acetate | 55 |
| Lavandin oil grosso | 20 |
| Lilial Givaudan-Roure | 10 |
| Linalool | 75 |
| Linalyl acetate | 100 |
| Orange oil white | 100 |
| Patchouli oil colourless | 10 |
| Sandolen H&R | 10 |
| Vertocitral H&R | 5 |

*Triethyl citrate a) The addition of 30 g of decahydro-2-ethoxy-2,3a,4,4,7-pentamethyl-3,7a-methano-7aH-indeno[5,6-b]furan serves to add to the masculine freshness of the perfume with a powdery-woody note and fixes the woody component of the fragrance.

b) The addition of 80 g of decahydro-2-ethoxy-2,3a,4,4,7-pentamethyl-3,7a-methano-7aH-indeno[5,6-b]furan serves to emphasize the woody component of the perfume composition, and the tenacity is significantly increased.

Example 2

Preparation of Decahydro-2-methoxy-2,3a,4,4,7-pentamethyl-3,7a-methano-7aH-indeno[5,6-b]furan (Isomeric Mixture of the Tetracyclic Acetals where R=Methyl):

10 g of decahydro-2-methylene-3 a,4,4,7-tetramethyl-3,7a-methano-7aH-indeno-[5,6-b]furan (prepared from alpha-cedrene and acetic anhydride in the presence of aluminum trichloride as in J. Chem. Soc. Perkin Trans. I 1983, pp. 1373–78) were dissolved in 100 g of methanol and left to stand for 48 h at room temperature. After the addition of a little bicarbonate, the methanol was stripped off at a temperature of at most 30°. The residue which remained was a mixture of the two isomeric acetals where R=methyl. To determine the structure, the isomers were separated by liquid chromatography on basic aluminum oxide.

$^1$H-NMR spectrum (400 MHz; $C_6D_6$; TMS=0 ppm):
Isomer A:
3.85 (dd, J=6.6, 1.3, 1H); 3.83 (s, 3H, O—CH3); 1.51 (s, 3H); 1.1 (s, 3H); 0.94 (s, 3H); 0.84 (d, J=7.3; 3H); 0.75 (s, 3H).
Isomer B:
3.81 (dd, J=7.4, 1.5; 1H); 3.30 (s, 3H, O—CH3); 1.41 (s, 3H); 1.40 (s, 3H); 0.96 (s, 3H); 0.77 (s, 3H); 0.73 (d, J=7.3; 3H).
Mass spectrum:
Isomer A: 263 (4, M$^+$-15);246 (30); 204 (18); 161(26); 119(100); 43(54).
Isomer B: 263 (4, M$^+$-15);246 (20); 204 (26); 161(34); 119(100); 43(48).

Example 3

Preparation of Decahydro-2-ethoxy-2,3a,4,4,7-pentamethyl-3,7a-methano-7aH-in-deno[5,6-b]furan (Isomeric Mixture of the Tetracyclic Acetals where R=Ethyl):

5 g of 1-(octahydro-8-hydroxy-3,6,7,7-tetramethyl-3a,6-ethano-3aH-inden-5-yl)-ethanone (prepared from alpha-cedrene and acetic anhydride in the presence of aluminum trichloride as in J. Chem. Soc. Perkin Trans. I 1983, pp. 1373–78) were admixed with 50 g of ethanol and refluxed for 10 min. After cooling, a little bicarbonate was added and the ethanol was stripped off at a temperature of at most 30°.

The residue which remained was a mixture of the two isomeric acetals where R=ethyl. To determine the structure, the isomers were separated by liquid chromatography on basic aluminum oxide.

$^1$H-NMR spectrum (400 MHz; $C_6D_6$; TMS=0 ppm):
Isomer A:
3.83 (qd, J=9.2, 7.1; 1H); 3.53 (qd, J=9.2, 7.0; 1H);1.45 (s, 3H); 1.42 (s, 3H); 1.19 (t, J=7,1; 3H); 0.74 (d, J=7.3; 3H); 0.98 (s, 3H); 0.78 (s, 3H).
Isomer B:
3.91 (qd, J=9.2, 7.1; 1H); 3.55 (qd, J=9.2, 7.0; 1H); 1.54 (s, 3H); 1.11 (s, 3H); 119 (t, J=7.1; 3H); 0.87 (d, 3=7.3; 3H); 0.95 (s, 3H); 0.76 (s, 3H).
Mass spectrum:
Isomer A: 277 (3, M$^+$-15);246 (22); 204 (18); 161(27); 119(100); 43(62).
Isomer B: 277 (3, M$^+$-15);246 (14); 204 (22); 161(38); 119(100); 43(60).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound comprising the structure I, in which R is a straight-chain or branched alkyl or alkenyl group having from 1 to 5 carbon atoms and at most one double bond,

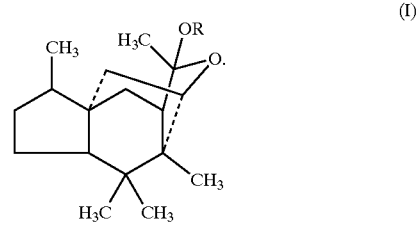

(I)

2. A compound according to claim 1, wherein said compound is 2-Alkoxydecahydro-2,3a,4,4,7-pentamethyl-3,7a-methano-7aH-indeno[5,6-b]furan.

3. A process for the preparation of 2-alkoxydecahydro-2,3a,4,4,7-pentamethyl-3,7a-methano-7aH-indeno[5,6-b]furans comprising the step of reacting decahydro-2-methylene-3a,4,4,7-tetramethyl-3,7a-methano-7aH-indeno[5,6-b]furan or 1-(octahydro-8-hydroxy-3,6,7,7-tetramethyl-3a,6-ethano-3aH-in-den-5-yl)-ethanone with at least one alcohol.

4. A fragrance comprising a compound having the structure I, in which R is a straight-chain or branched alkyl or alkenyl group having from 1 to 5 carbon atoms and at most one double bond,

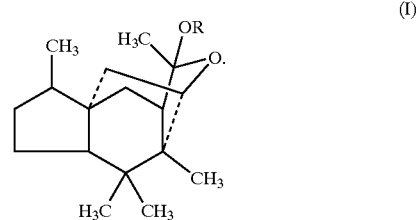

(I)

5. A fragrance according to claim 4, wherein said compound is 2-Alkoxydeca-hydro-2,3a,4,4,7-pentamethyl-3,7a-methano-7aH-indeno[5,6-b]furan.

6. A perfume oil comprising a compound having the structure I, in which R is a straight-chain or branched alkyl or alkenyl group having from 1 to 5 carbon atoms and at most one double bond.

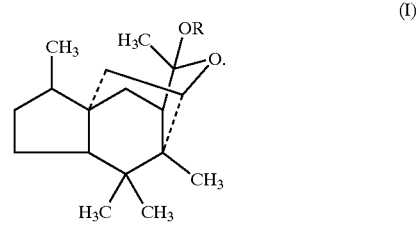

(I)

7. A perfume oil according to claim 6, wherein said compound is 2-Alkoxydecahydro-2,3a,4,4,7-pentamethyl-3,7a-methano-7aH-indeno[5,6-b]furan.

* * * * *